US012274715B2

(12) United States Patent
Cho

(10) Patent No.: US 12,274,715 B2
(45) Date of Patent: Apr. 15, 2025

(54) METHOD FOR MAXIMIZING CORONAVIRUS KILLING ACTIVITY OF HIGH-DENSITY LIPOPROTEINS, AND PHARMACEUTICAL COMPOSITION FOR PREVENTING OR TREATING COVID-19

(71) Applicant: RAYDEL KOREA CO., LTD., Seoul (KR)

(72) Inventor: Kyung-Hyun Cho, Daegu (KR)

(73) Assignee: Raydel Korea Co., Ltd., Seoul (KR)

( * ) Notice: Subject to any disclaimer, the term of this patent is extended or adjusted under 35 U.S.C. 154(b) by 0 days.

(21) Appl. No.: 18/253,999

(22) PCT Filed: Dec. 22, 2021

(86) PCT No.: PCT/KR2021/019587
§ 371 (c)(1),
(2) Date: May 23, 2023

(87) PCT Pub. No.: WO2022/154297
PCT Pub. Date: Jul. 21, 2022

(65) Prior Publication Data
US 2023/0390333 A1 Dec. 7, 2023

(30) Foreign Application Priority Data
Jan. 13, 2021 (KR) .......... 10-2021-0004421

(51) Int. Cl.
*A61K 35/16* (2015.01)
*A61P 31/14* (2006.01)
*C12Q 1/44* (2006.01)
*G01N 33/92* (2006.01)

(52) U.S. Cl.
CPC .............. *A61K 35/16* (2013.01); *A61P 31/14* (2018.01); *C12Q 1/44* (2013.01); *G01N 33/92* (2013.01); *G01N 2333/775* (2013.01); *G01N 2440/38* (2013.01); *G01N 2800/26* (2013.01); *G01N 2800/52* (2013.01)

(58) Field of Classification Search
None
See application file for complete search history.

(56) References Cited

U.S. PATENT DOCUMENTS

| 2005/0043408 A1* | 2/2005 | Yeboah ............... A61P 3/10 514/567 |
| 2018/0015171 A1* | 1/2018 | Suda ............... A61K 47/64 |

FOREIGN PATENT DOCUMENTS

| KR | 10-2011-0020540 | | 3/2011 |
| KR | 1020090078207 | | 3/2011 |
| WO | WO-2013100292 A1 * | 7/2013 | ............. A61K 38/16 |
| WO | 2021/191266 | | 9/2021 |

OTHER PUBLICATIONS

Sharma et al. Viruses 2021, 13;202:1-25. (Year: 2021).*
Morin et al. Frontiers in Pharmacology, 2015, 6;244: 1-10. (Year: 2015).*
Waksman et al. Journal of the American College of Cardiology. 2010, 55;24:2727-2735. (Year: 2010).*
Brewer Jr. et al. Journal of Clinical Lipidology 2024, 18, e374-e383. (Year: 2024).*
Fazio et al. Circ. Res. 2016, 119(6):704-707. (Year: 2016).*
Catte et al. Biophysical Journal 2008, 94:2306-2319. (Year: 2008).*
Oravec et al. Neuroendocrinology Letters 2011, 32(4):502-509. (Year: 2011).*
Hamilton et al. Critical Care 2023, 27(389):1-19. (Year: 2023).*
Written Opinion of the International Searching Authority in PCT/KR2021/019587 dated Apr. 5, 2022.
Rabaan et al. "SARS-CoV-2, SARS-CoV, and MERS-CoV: a comparative overview" Le Infezioni in Medicina 2020 2:174-184.
Wang et al. "Low high-density lipoprotein level is correlated with the severity of COVID-19 patients : an observational study" Lipids in Health and Disease 2020 19:204.
Wei et al. "HDL-scavenger receptor B type 1 facilitates SARS-CoV entry" Nature metabolism Dec. 2020; 2 (12) : 1391-1400.
Cho et al. "Myocardial infarction patients show altered lipoprotein properties and functions when compared with stable angina pectoris patients" Experimental and Molecular Medicine 2009 41 (2) : 67-76.
Sorokin et al. "COVID-19—Associated dyslipidemia: Implications for mechanism of impaired resolution and novel therapeutic approaches" The FASEB Journal 2020 34: 9843-9853.
Jairajpuri, D.S. & Jairajpuri, Z.S. "Isoferulic Acid Action against Glycation-Induced Changes sin Structural and Functional Attributes of Human High Density Lipoprotein" Biochemistry (Moscow) 2016 81(3): 289-295.
Singh et al. "Lipoproteins account for part of the broad non-specific antiviral activity of human serum" Antiviral Research 1999 42 (3): 211-218.

(Continued)

*Primary Examiner* — Chun W Dahle
(74) *Attorney, Agent, or Firm* — Licata & Tyrrell P.C.

(57) ABSTRACT

The present invention relates a method for maximizing the coronavirus killing activity of high-density lipoproteins, and a pharmaceutical composition for preventing or treating COVID-19. As identified by the present inventors, non-glycated normal high-density lipoproteins (HDLs) exhibit killing activity against coronavirus (SARS-Cov-2) that is superior to that of glycated HDLs, and thus a pharmaceutical composition for preventing and treating COVID-19, containing non-glycated native HDLs as an active ingredient, is provided. In addition, the present invention is useful since a method for maximizing the coronavirus killing activity by using an HDL glycation inhibitor, on the basis of the identification by the present inventors, can be provided and a method for screening for a pharmaceutical composition for preventing and treating COVID-19 by evaluating the degree of HDL glycosylation inhibition of candidate drugs can be provided.

2 Claims, 9 Drawing Sheets

(56) References Cited

OTHER PUBLICATIONS

Henrich et al. "Targeting Scavenger Receptor Type B-1 (SR-B1) and Cholesterol Inhibits Entry of SARS-COV-2 Pseudovirus in Cell Culture" BioRxiv 2020 10 pages.

Hedrick et al. "Glycation impairs high-density lipoprotein function" Diabetologia 2000 43:312-320.

"Induction of senescence by glycated high-density lipoprotein (HDL) and prevention of aging by enhancing HDL" Core Research Project Final Report, Yeungnam University 2012.

Bacchetti et al. "Glycation of human high density lipoprotein by methylglyoxal: Effect on HDL-paraoxonase activity" Metabolism 2014 63(3) : 307-311.

Kjerulf et al. "Glycation of HDL blunts its anti-inflammatory and cholesterol efflux capacities in vitro, but has no effect in poorly controlled type 1 diabetes subjects" Journal of Diabetes and Its Complications 2020 34 (12) : 10 pages.

Lemmers et al. "The anti-inflammatory function of high-density lipoprotein in type II diabetes: A systematic review", Journal of Clinical Lipidology 2017 11(3): 712-724.

Liu et al. "Nonenzymatic glycation of high-density lipoprotein impairs its anti-inflammatory effects in innate immunity", Diabetes/Metabolism Research and Reviews 2012 28 (2) : 186-195.

Faguer et al. "Apolipoprotein-A-I for severe COVID-19-induced hyperinflammatory states: A prospective case study" Front Pharmacol. 2022 8 pages.

Kluck et al. "Good Cholesterol Gone Bad? HDL and COVID-19" Int J Mol Sci. 2021 22 (19) : 10182 22 pages.

\* cited by examiner

METHOD FOR MAXIMIZING CORONAVIRUS KILLING ACTIVITY OF HIGH-DENSITY LIPOPROTEINS, AND PHARMACEUTICAL COMPOSITION FOR PREVENTING OR TREATING COVID-19

CROSS-REFERENCES TO RELATED APPLICATION

This patent application is the National Stage of International Application No. PCT/KR2021/019587 filed Dec. 22, 2021, which claims the benefit of priority under 35 U.S.C. § 119 from Korean Patent Application 10-2021-0004421 filed on Jan. 13, 2021, the contents of each of which are incorporated herein by reference in their entirety.

BACKGROUND OF THE INVENTION

1. Field of the Invention

The present invention relates a method for maximizing the coronavirus killing activity of high-density lipoproteins, and a pharmaceutical composition for preventing or treating COVID-19.

2. Description of the Related Art

COVID-19, which occurred in Wuhan, Hubei Province, China in December 2019, had spread to about 114 countries by March 2020. Accordingly, the World Health Organization (WHO) declared that COVID-19 is a global pandemic situation. Since then, by September 2020, about 35 million infected patients have occurred worldwide, of which about 1 million have died, and the number of infected patients and deaths continues to increase.

COVID-19 shows respiratory symptoms such as dry cough, sputum, and difficulty in breathing along with fever, and can cause complications such as acute dyspnea syndrome, heart failure, and arrhythmia. In this case, conservative treatment is being conducted through oxygen therapy, and administration of antiviral agents and antibiotics, but there is a problem that sufficient effect does not appear because it is not a cure for coronavirus.

COVID-19 is mainly infected by the spread of droplets caused by coughing or sneezing, and the basic reproduction number (average number of people infected by one infected person during contagious period) is 2 to 2.5, which is known to be more contagious than the flu. In addition, in the case of COVID-19, even asymptomatic infected people can spread the virus, making it difficult to effectively block the virus.

Meanwhile, coronavirus (CoV) phylogenetically refer to a virus belonging to Coronaviridae, and the subgroup Ortho Coronaviridae is classified into four genera: alpha-CoV, beta-CoV, delta-CoV, and gamma-CoV. Among them, only alpha-CoV and beta-CoV infect mammals, while delta-CoV and gamma-CoV infect birds and some mammals.

So far, there are seven types of coronavirus (HCoV) that can infect humans: HCoV-229E and HCoV-NL63 of alpha-CoV, HCoV-OC43, HCoV-HKU1, SARS-CoV and MERS-CoV of beta-CoV, and SARS-CoV-2, the causative agent of the 2019 coronavirus disease (COVID-19). HCoV-229E, HCoV-NL63, HCoV-OC43 and HCoV-HKU1 cause common colds or gastrointestinal diseases in humans, but along with SARS-CoV and MERS-CoV, SARS-CoV-2 causes severe acute respiratory infectious diseases.

SARS-CoV-2 belongs to beta-CoV in the phylogenetic tree along with SARS-CoV and MERS-CoV, but it is clearly distinct from SARS-CoV in terms of molecular phylogeny and evolved quite a long time ago from MERS-CoV, which has about half of its nucleotide sequence similarity, as shown in the evolutionary analysis of SARS-CoV, MERS-CoV and SARS-CoV-2 using the maximum likelihood method (Evolutionary analysis of SARS-CoV, MERS-CoV-2 and SARS-CoV-2, Maximum Likelihood).

In addition, SARS-CoV-2 has some similarities in structure and pathogenicity compared to SARS-CoV, but there is a clear structural difference in the protein structure, that is, the spike protein (S), which should be considered most important for vaccine development. The presence of a furin-like cleavage site (SLLR-ST) in SARS-CoV-2 promotes priming of S protein, further increasing transmissibility of SARS-CoV-2 compared to SARS-CoV (Non-patent reference 1, Le Infezioni in Medicina, n. 2, 174-184, 2020, SARS-CoV-2, SARS-CoV, and MERS-CoV: a comparative overview).

More specifically, cleavage of the S protein of MERS-CoV by RSVR↓SV is mediated by furin during viral egress, whereas the S protein of SARS-CoV is not completely cleaved because SARS-CoV lacks a furin-like cleavage site (SLLR-ST). In MERS-CoV, S protein cleavage occurs at the conserved sequence AYT↓M by the protease (elastase, cathepsin L or TMPRS) expressed by target cells. On the other hand, the S protein of SARS-CoV-2 has 12 additional nucleotides upstream of a single Arg↓ cleavage site 1 forming the PRRAR↓SV sequence, which corresponds to the furin-like cleavage site (SLLR-ST). As described above, the presence of a furin-like cleavage site (SLLR-ST) in SARS-CoV-2 promotes priming of the S protein, and furthermore, enhances SARS-CoV-2 transmissibility compared to SARS-CoV. That is, there is a clear structural difference between SARS-CoV-2 and SARS-CoV.

In addition, the RNA nucleotide sequence of SARS-CoV-2 has a clear difference compared to the RNA nucleotide sequences of the existing SARS-CoV and MERS-CoV. For example, the RNA nucleotide sequence of SARS-CoV-2 differs by 17.7% from the RNA nucleotide sequence of the existing SARS-CoV. It is clear that the difference is such a significant difference that the existing SARS-CoV treatment cannot be used as it is for the prevention and treatment of SARS-CoV-2, and the development of a new vaccine for SARS-CoV-2 is absolutely necessary.

On the other hand, there have been recent reports that the levels of total cholesterol, HDL-cholesterol and LDL-cholesterol in the blood of COVID-19 patients are generally lower than those of normal people, and that the severity of COVID-19 disease is higher in patients with lower levels of HDL-cholesterol (Wang et al. Lipids in Health and Disease (2020) 19:204). However, another report suggested that when coronavirus (SARS-Co-V-2) enters cells, it binds to HDL cholesterol and enters cells through SR-B-1, a receptor of HDL (Nature metabolism 2020 Nov. 26 in nature.com/articles/s42255-020-00324-0 of www), Therefore, to date, the function and role of HDL in COVID-19 infection are not clear. In addition, the above reports are only early-stage level reports of observing COVID-19 patients based on various indicators of blood compared to normal people, and research and development in various ways are needed in that they have not yet revealed a direct relationship or function with COVID-19 disease.

Under the above background, the present inventors first confirmed the ability to the coronavirus (SARS-Co-V-2) killing activity of native HDL (high-density lipoprotein)

isolated from human serum through ultracentrifugation. In addition, the present inventors produced glycated HDL from native HDL through fructose treatment and examined the changes in the structure and function of HDL due to glycation, and confirmed that the structure and shape of native HDL are changed by glycation and the activity of paraoxonase is inhibited by glycation through electron microscopic observation. The present inventors also confirmed for the first time that the ability to kill coronavirus also decreases as the structure and function of HDL are damaged by glycation of HDL. Accordingly, the present inventors have completed the present invention by confirming that a pharmaceutical composition for preventing and treating corona19 disease (COVID-19) comprising HDL (high-density lipoprotein) as an active ingredient, a method for maximizing the coronavirus killing activity of HDL (high-density lipoprotein), and a screening method for developing drugs for preventing and treating corona19 disease (COVID-19) can be provided, based on the facts disclosed by the present inventors.

SUMMARY OF THE INVENTION

It is an object of the present invention to provide a pharmaceutical composition for preventing and treating corona 19 disease (COVID-19) having the ability to kill coronavirus (SARS-Co-V-2), a method for maximizing the coronavirus killing activity of HDL (high-density lipoprotein), and a screening method for developing drugs for preventing and treating corona19 disease (COVID-19).

To achieve the above object, the present invention provides a pharmaceutical composition for preventing and treating corona19 disease (COVID-19) comprising HDL (high-density lipoprotein) as an active ingredient.

The present invention also provides a method for maximizing the coronavirus killing activity of HDL (high-density lipoprotein) using an inhibitor of HDL (high-density lipoprotein) glycation.

The present invention also provides an HDL (high-density lipoprotein) glycation induction model, which is prepared by treating HDL (high-density lipoprotein) with any one or two or more sugar compounds selected from the group consisting of fructose, glucose and galactose.

The present invention also provides a method for screening a pharmaceutical composition for preventing or treating corona19 disease (COVID-19) consisting of the following steps:
  a step of evaluating by comparing the degree of glycation using the HDL glycation induction model as a control group and the HDL glycation induction model treated with a candidate drug as an experimental group; and
  a step of determining that the treated candidate drug is effective against COVID-19 when the degree of glycation is low in the experimental group treated with the candidate drug compared to the control group.

In addition, the present invention provides an information providing method for evaluating the prognosis of COVID-19 consisting of the following steps:
  a step of evaluating by comparing the degree of glycation using the HDL glycation induction model as a control group and the HDL isolated from the blood sample of the test subject as an experimental group; and
  a step of determining that the prognosis of COVID-19 is good when the degree of glycation in the experimental group HDL isolated from the blood sample is low compared to the control group.

Advantageous Effect

As identified by the present inventors, non-glycated normal high-density lipoproteins (HDLs) exhibit killing activity against coronavirus (SARS-Cov-2) that is superior to that of glycated HDLs, and thus a pharmaceutical composition for preventing and treating COVID-19, containing non-glycated native HDLs as an active ingredient, is provided. In addition, the present invention is useful since a method for maximizing the coronavirus killing activity by using an HDL glycation inhibitor, on the basis of the identification by the present inventors, can be provided and a method for screening for a pharmaceutical composition for preventing and treating COVID-19 by evaluating the degree of HDL glycosylation inhibition of candidate drugs can be provided.

DESCRIPTION OF THE PREFERRED EMBODIMENTS

Figure 1:
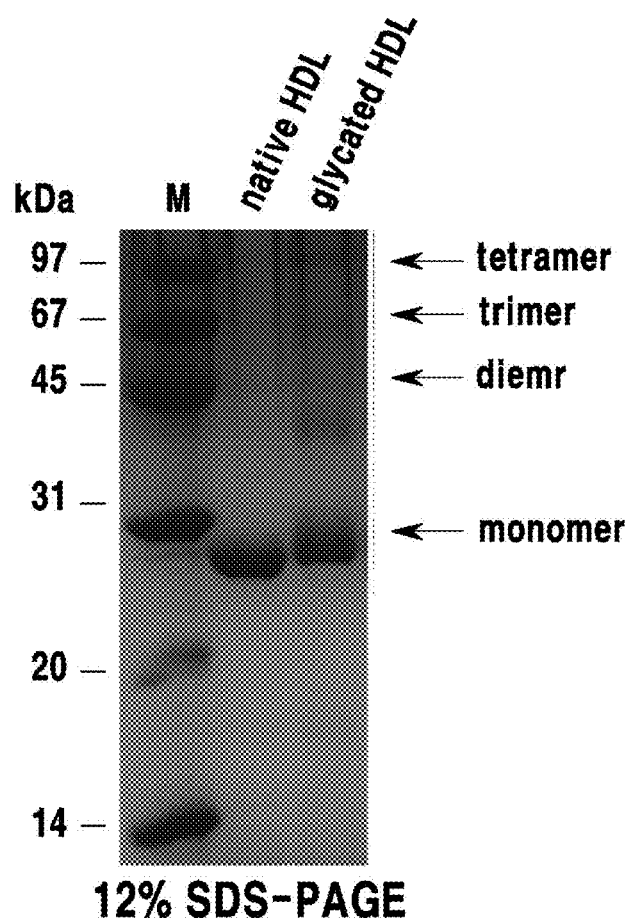
FIG. 1 is a photograph showing the electrophoretic patterns of native HDL and glycated HDL according to the present invention.

Hereinafter, the present invention is described in detail.

The present invention provides a pharmaceutical composition for preventing and treating corona19 disease (COVID-19) comprising HDL (high-density lipoprotein) as an active ingredient.

The HDL is non-glycated HDL and has the ability to kill coronavirus (SARS-Co-V-2). The HDL is non-glycated HDL, and has the ability to kill coronavirus (SARS-Co-V-2) from showing the normal function of HDL, for example, the HDL has the ability to kill coronavirus (SARS-Co-V-2) by the paraoxonase activity of HDL or the activity of preventing macrophage phagocytosis of acetylated LDL.

The present inventors compared and evaluated the structures, functions, and coronavirus (SARS-Co-V-2) killing activities of native HDL and HDL glycation induction model. As a result, it was confirmed that the normal structure and function of HDL were impaired in the HDL glycation induction model. In particular, native HDL exhibited excellent killing ability against coronavirus (SARS-Co-V-2), from which it has been confirmed that a pharmaceutical composition for preventing and treating corona19 disease (COVID-19) containing native HDL as an active ingredient can be provided.

In an embodiment of the present invention, native HDL (high-density lipoprotein) isolated from human serum through ultracentrifugation was prepared, a HDL glycation induction model was prepared by treating HDL with fructose, and the native HDL and HDL glycation induction model were analyzed with an electron microscope. As a result, it was confirmed that the native HDL had a large particle size of 18-21 nm in diameter and a clear structure and contour, while the glycated HDL had a modified particle structure due to glycation modification by fructose and oxidative stress, and a small particle size of 13-16 nm in diameter and a blurred structure and outline (see FIG. 3).

In an embodiment of the present invention, the paraoxonase activities of native HDL and HDL glycation induction model were compared and evaluated. As a result, the glycated HDL showed less than half of the paraoxonase activity compared to the native HDL, confirming that the function of HDL was impaired by glycation (see FIG. 4).

In an embodiment of the present invention, the prevention activity of native HDL and HDL glycation induction model against macrophage phagocytosis of acetylated LDL, which is an early response of atherosclerosis, was compared and evaluated. As a result, phagocytosis of LDL was reduced by more than 60% when native HDL was co-treated compared to when acetylated LDL was treated alone, while phagocytosis was increased by 1.3 times when glycated HDL was co-treated compared to when native HDL was treated, confirming that the function of HDL was impaired due to glycation (see FIG. 5).

In an embodiment of the present invention, the amount of oxides produced in cell culture media was compared and evaluated for native HDL and HDL glycation induction model by thiobarbituric acid reaction quantification method. As a result, the highest MDA (malondialdehyde) of 3.8 nM was detected when acetylated LDL was treated, while the lowest MDA of 1.3 nM was detected when native HDL was co-treated, and 2.8 nM of MDA was detected when glycated HDL was co-treated, confirming that the function of HDL was impaired by glycation (see FIG. 6).

In an embodiment of the present invention, the cytotoxicity was compared and evaluated for native HDL and HDL glycation induction model. As a result, As a result, native HDL showed a cell viability of 68-73%, whereas glycated HDL showed a cell viability of 40-49%, confirming that the cytotoxicity of HDL was increased by glycation (see FIG. 7).

In an embodiment of the present invention, the ability to kill coronavirus (SARS-Co-V-2) was compared and evaluated for native HDL and HDL glycation induction model. As a result, native HDL showed 62% killing ability, while glycated HDL showed 17% killing ability, confirming that the ability of HDL to kill coronavirus (SARS-Co-V-2) was impaired by glycation. In addition, it was confirmed that native HDL exhibited 3.6 times higher ability to kill coronavirus (SARS-Co-V-2) than glycated HDL (see FIG. 8).

Therefore, non-glycated native HDL (high-density lipoprotein) did not exhibit impairment in the structure and function of HDL and exhibited excellent killing ability against coronavirus (SARS-Co-V-2), from which a pharmaceutical composition for the preventing and treating corona19 disease (COVID-19) comprising native HDL as an active ingredient can be provided.

The present invention also provides a method for maximizing the coronavirus killing activity of HDL (high-density lipoprotein) using an inhibitor of HDL (high-density lipoprotein) glycation.

The HDL glycation inhibitor can prevent the reduction in the killing ability of HDL against coronavirus (SARS-Co-V-2) due to the structural and functional damage of HDL by inhibiting glycation of HDL, and can also maximize the killing ability of HDL against coronavirus (SARS-Co-V-2) from the inhibition of HDL glycation.

The present invention also provides an HDL (high-density lipoprotein) glycation induction model, which is prepared by treating HDL (high-density lipoprotein) with any one or two or more sugar compounds selected from the group consisting of fructose, glucose and galactose.

The sugar compounds can be treated at or above a concentration to maximally saturate HDL glycation. In addition, the sugar compound treatment may preferably be fructose treatment.

In an embodiment of the present invention, HDL was isolated from human serum by ultracentrifugation, and an HDL glycation induction model was prepared by treating the isolated HDL with an excessive amount of fructose (5 mM-250 mM/1-10 mg/ml of HDL) for 72 hours. It was confirmed by electrophoresis that the HDL glycation induction model was produced, and apoA-I with increased molecular weight was observed in the glycated HDL, and it was confirmed that multimerized HDL such as dimer~tetramer was produced (see FIG. 1). In addition, it was confirmed that an HDL glycation induction model was successfully produced by confirming the fluorescence intensity increased 7 times in the HDL glycation induction model compared to native HDL (see FIG. 2).

The present invention also provides a method for screening a pharmaceutical composition for preventing or treating corona19 disease (COVID-19) consisting of the following steps:

a step of evaluating by comparing the degree of glycation using the HDL glycation induction model as a control group and the HDL glycation induction model treated with a candidate drug as an experimental group; and a step of determining that the treated candidate drug is effective against COVID-19 when the degree of glycation is low in the experimental group treated with the candidate drug compared to the control group.

The step of evaluating by comparing the degree of glycation may be to compare and evaluate the degree of glycation by detecting and quantifying a fluorescent signal caused by glycation.

Figure 2:
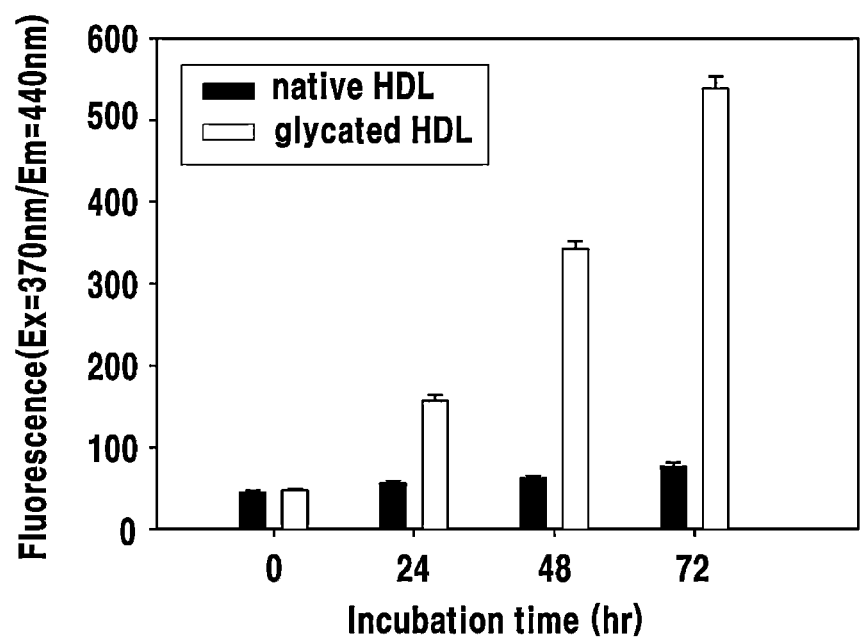
FIG. 2 is a graph showing the results of fluorescence analysis of native HDL and glycated HDL.

In an embodiment of the present invention, the degree of glycation in the HDL glycation induction model compared to native HDL was quantitatively measured and evaluated by confirming the fluorescence intensity increased 7-fold in the HDL glycation induction model compared to native HDL (see FIG. 2).

According to the judgment that the candidate drug is effective for COVID-19 when the degree of glycation of the experimental group treated with the candidate drug is lower than that of the control group, a drug that inhibits glycation of native HDL can be understood as a drug to prevent damage to the ability of HDL to kill coronavirus (SARS-Co-V-2).

In an embodiment of the present invention, the killing ability of native HDL and HDL glycation induction model against coronavirus (SARS-Co-V-2) was compared and evaluated. As a result, native HDL showed 62% killing ability, while glycated HDL showed 17% killing ability, confirming that the killing ability of HDL against coronavirus (SARS-Co-V-2) was impaired by glycation.

Therefore, an HDL glycation inhibitor that prevents damage to the killing ability of HDL against coronavirus (SARS-Co-V-2) by glycation and maximizes the killing ability can be screened as an effective ingredient for preventing or treating corona19 infection (COVID-19).

The step of evaluating by comparing the degree of glycation of HDL may further include a step of comparing and evaluating at least one activity of paraoxonase activity of HDL and activity of HDL to prevent macrophage phagocytosis of acetylated LDL.

If at least one of the paraoxonase activity of HDL and the activity of HDL to prevent macrophage phagocytosis of acetylated LDL is high in the experimental group treated with the candidate drug compared to the HDL glycation induction model control group, the treated candidate drug can be determined to be effective against corona19 infection (COVID-19).

In an embodiment of the present invention, the paraoxonase activity of native HDL and HDL glycation induction model was compared and evaluated. As a result, glycated HDL showed the paraoxonase activity less than half of that of native HDL, confirming that the function of HDL was impaired by glycation (see FIG. 4).

In an embodiment of the present invention, the activity of native HDL and HDL glycation induction model to prevent macrophage phagocytosis of acetylated LDL was compared and evaluated. As a result, the phagocytosis of LDL was decreased by more than 60% when native HDL was co-treated than when acetylated LDL was treated alone, while the phagocytosis was increased by 1.3 times when glycated HDL was co-treated than when native HDL was treated, confirming that the function of HDL was impaired by glycation (see FIG. 5).

Therefore, an HDL glycation inhibitor that prevents damage to the paraoxonase activity of HDL and the activity of HDL to prevent macrophage phagocytosis of acetylated LDL by glycation, and maximizes the killing ability of HDN against coronavirus (SARS-Co-V-2) can be screened as an effective ingredient for preventing or treating corona19 infection (COVID-19).

In addition, the present invention provides an information providing method for evaluating the prognosis of COVID-19 consisting of the following steps:
  a step of evaluating by comparing the degree of glycation using the HDL glycation induction model as a control group and the HDL isolated from the blood sample of the test subject as an experimental group; and
  a step of determining that the prognosis of COVID-19 is good when the degree of glycation in the experimental group HDL isolated from the blood sample is low compared to the control group.

The step of evaluating by comparing the degree of glycation may be to compare and evaluate the degree of glycation by detecting and quantifying a fluorescent signal caused by glycation.

In an embodiment of the present invention, the degree of glycation in the HDL glycation induction model compared to native HDL was quantitatively measured and evaluated by confirming the fluorescence intensity increased 7-fold in the HDL glycation induction model compared to native HDL (see FIG. 2).

The prognosis of COVID-19 is judged to be good when the degree of glycation of the experimental group HDL isolated from the blood sample is lower than that of the HDL glycation induction model control group. This is based on the judgment that there is no damage to the killing ability of HDL against coronavirus (SARS-Co-V-2 by glycation, and that the ability of native HDL to kill coronavirus (SARS-Co-V-2 is maintained.

In an embodiment of the present invention, the killing ability of native HDL and HDL glycation induction model against coronavirus (SARS-Co-V-2) was compared and evaluated. As a result, native HDL showed 62% killing ability, while glycated HDL showed 17% killing ability, confirming that the killing ability of HDL against coronavirus (SARS-Co-V-2) was impaired by glycation.

Therefore, by confirming that there is no or less glycation of HDL compared to the control group, it can be confirmed that there is no or less damage to the ability of HDL to kill coronavirus (SARS-Co-V-2) by glycation, so it can be judged that the prognosis of COVID-19 is good.

The step of evaluating by comparing the degree of glycation of HDL may further include a step of comparing and evaluating at least one activity of paraoxonase activity of HDL and activity of HDL to prevent macrophage phagocytosis of acetylated LDL.

If at least one of the paraoxonase activity of HDL and the activity of HDL to prevent macrophage phagocytosis of acetylated LDL is high in the experimental group HDL isolated from the blood sample compared to the HDL glycation induction model control group, it can be determined that the prognosis of COVID-19 is good.

In an embodiment of the present invention, the paraoxonase activity of native HDL and HDL glycation induction model was compared and evaluated. As a result, glycated HDL showed the paraoxonase activity less than half of that of native HDL, confirming that the function of HDL was impaired by glycation (see FIG. 4).

In an embodiment of the present invention, the activity of native HDL and HDL glycation induction model to prevent macrophage phagocytosis of acetylated LDL was compared and evaluated. As a result, the phagocytosis of LDL was decreased by more than 60% when native HDL was co-treated than when acetylated LDL was treated alone, while the phagocytosis was increased by 1.3 times when glycated HDL was co-treated than when native HDL was treated, confirming that the function of HDL was impaired by glycation (see FIG. 5).

Therefore, by confirming that the paraoxonase activity of HDL and the activity of HDL to prevent macrophage phagocytosis of acetylated LDL are not impaired or less than the control group, it can be confirmed that there is no or less damage to the ability of HDL to kill coronavirus (SARS-Co-V-2) by glycation, so it can be judged that the prognosis of COVID-19 is good.

Hereinafter, the present invention will be described in detail by the following examples and experimental examples.

However, the following examples and experimental examples are only for illustrating the present invention, and the contents of the present invention are not limited thereto.

Example 1: Preparation of Native HDL

Native HDL was isolated from human plasma through ultracentrifugation (100,000 g) for 48-72 hours according to the method suggested by the prior paper of the present inventors (Cho, K.-H.; Shin, D.-G.; Baek, S.-H.; Kim, J.-R. Myocardial infarction patients show altered lipoprotein properties and functions when compared with stable angina pectoris patients. *Exp Mol Med* 2009, 41, 67-76, doi: 10.3858/emm.2009.41.2.009.).

Example 2: Preparation of HDL Glycation Induction Model

An HDL glycation induction model was prepared by treating some of the human serum-derived HDL prepared in Example 1 with an excess of fructose.

Specifically, the purified HDL (1-10 mg/mL) was reacted with 5 mM~250 mM D-fructose [in 200 mM potassium phosphate/0.02% sodium azide buffer (pH 7.4)] for 24~72 hours at 37° C. in air containing 5% $CO_2$.

After the glycation reaction, HDL was compared and confirmed by 12% SDS-PAGE in which electrophoretic separation occurs according to the molecular weight of the protein. As a result, as shown in FIG. 1, in glycated HDL, apoA-I with increased molecular weight was observed, and a number of multimerized HDL such as dimers and tetramers were confirmed.

On the other hand, the degree of glycation of the HDL glycation induction model was determined by measuring the fluorescence intensity of the produced fluorescent substance at 370 nm (excitation) and 440 nm (emission), and the results are shown in FIG. 2.

As shown in FIG. 2, by the fructose treatment for 72 hours, the fluorescence intensity of the HDL glycation induction model was increased by about 7 times compared to native HDL, confirming that the HDL glycation induction model was successfully constructed.

Experimental Example 1: Evaluation of Structural Changes in HDL by Glycation

The structural changes in HDL caused by glycation were evaluated by analyzing the structural differences between native HDL and HDL glycation induction model.

Figure 3:
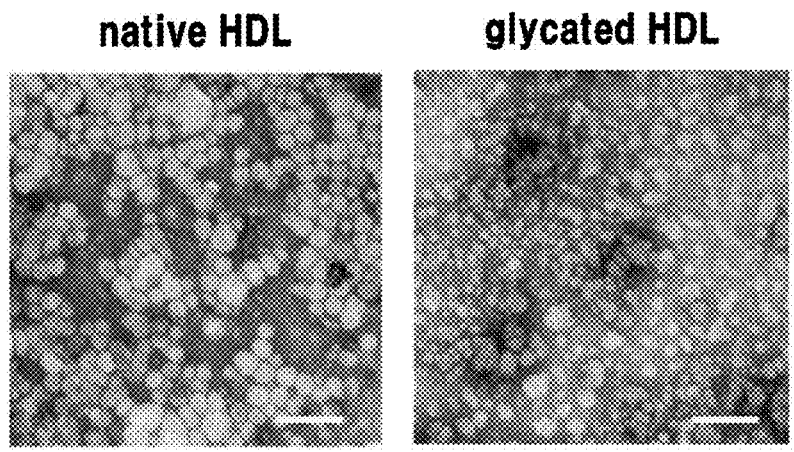
FIG. 3 is a set of electron micrographs showing the structures of native HDL and glycated HDL.

Specifically, the protein concentration of native HDL and HDL glycation induction model was adjusted to 0.3 mg/mL, stained with 1% sodium phosphotungstate, and observed under a high voltage of 80 kV using a transmission electron microscope (Hitachi HT-7800, 40,000×), and the photographs are shown in FIG. 3.

As shown in FIG. 3, it was confirmed that native HDL had a large particle size of 18-21 nm in diameter and a clear structure and outline, whereas glycated HDL had a small particle size of 13-16 nm in diameter and a blurred structure and outline. These results indicate that the glycation modification and oxidative stress caused by fructose treatment caused the cleavage and aggregation of apoA-I and modified the particle structure of HDL.

Experimental Example 2: Evaluation of Functional Changes in HDL by Glycation

By analyzing the functional differences between the native HDL prepared in Example 1 and the HDL glycation induction model prepared in Example 2, the functional changes in HDL by glycation was evaluated.

<2-1> Analysis of Paraoxonase Activity

By analyzing the difference in paraoxonase activity between native HDL and HDL glycation induction model, the functional change in HDL by glycation was evaluated.

The activity of paraoxonase, a major enzyme responsible for the antioxidant function of HDL, was measured as follows. The activity of paraoxonase was evaluated by measuring the absorbance at 415 nm of p-nitrophenol produced in an enzyme solution (90 mM Tris-HCl/3.6 mM NaCl/2 mM $CaCl_2$) [pH 8.5]) by reacting with native HDL and HDL glycation induction model, respectively, using paraoxon-ethyl as a substrate, and the results are shown in FIG. 4.

Figure 4:
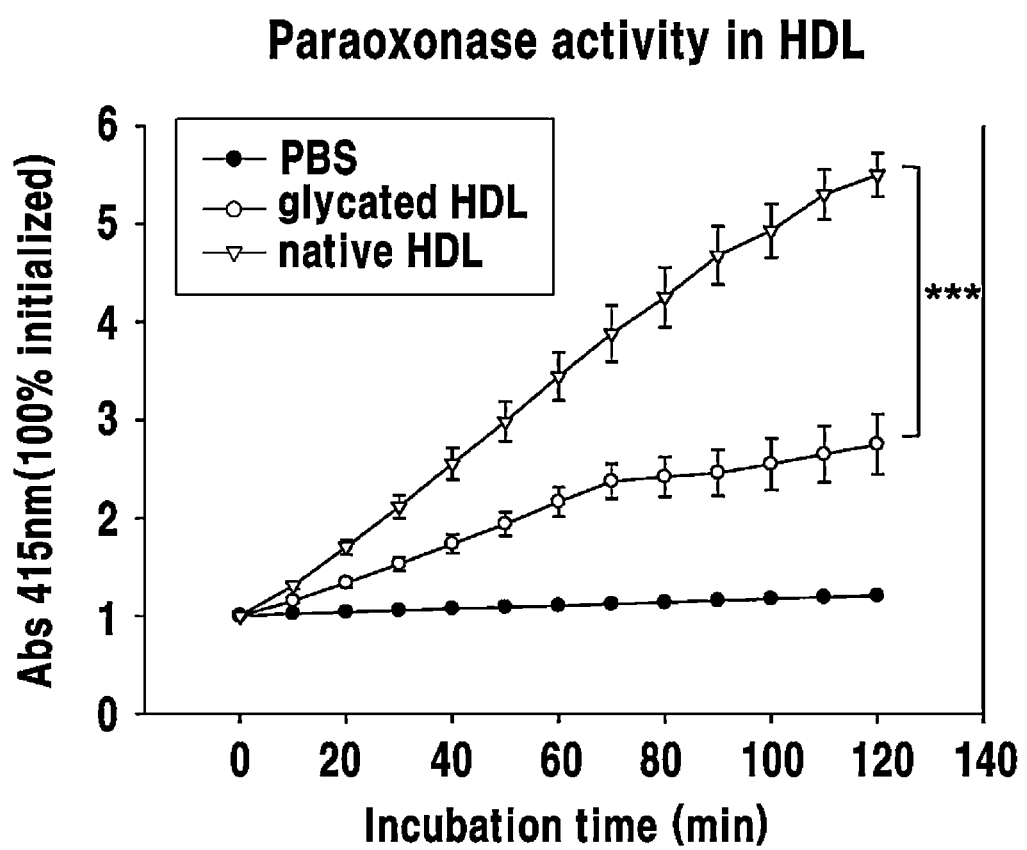
FIG. 4 is a graph showing the comparison of paraoxonase activity of native HDL and glycated HDL.
Figure 5A:
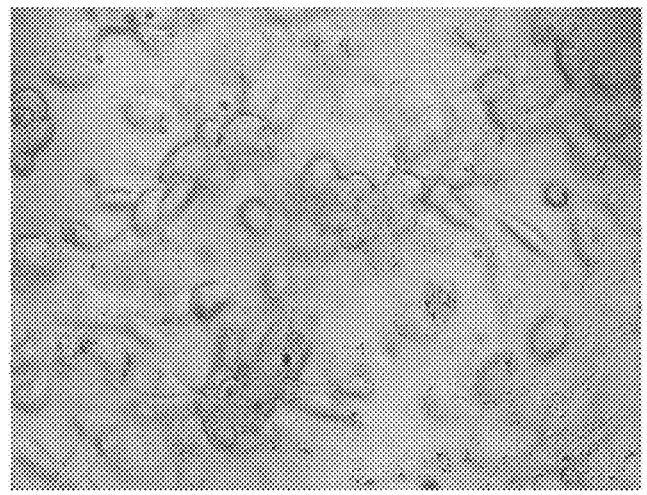
FIG. 5A is a photograph showing the normal macrophages.
Figure 5B:
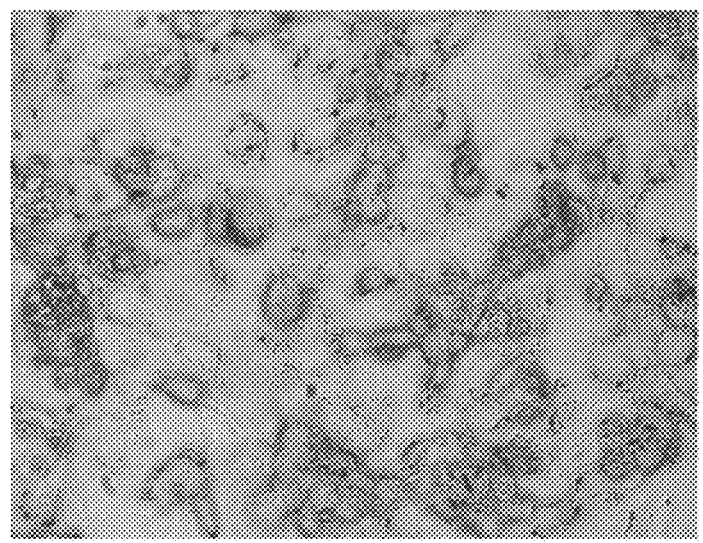
FIG. 5B is a photograph showing the macrophage phagocytosis of acetylated LDL.
Figure 5C:
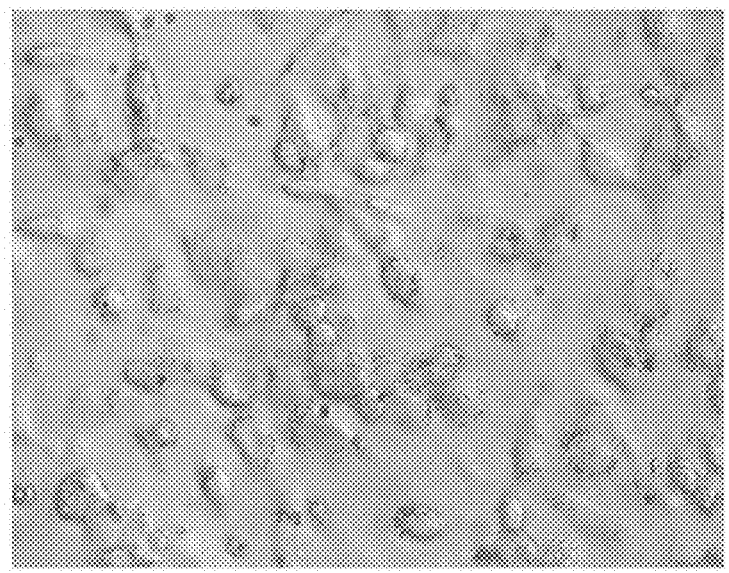
FIG. 5C is a photograph showing the macrophage phagocytosis of acetylated LDL inhibited by co-treatment of native HDL.
Figure 5D:
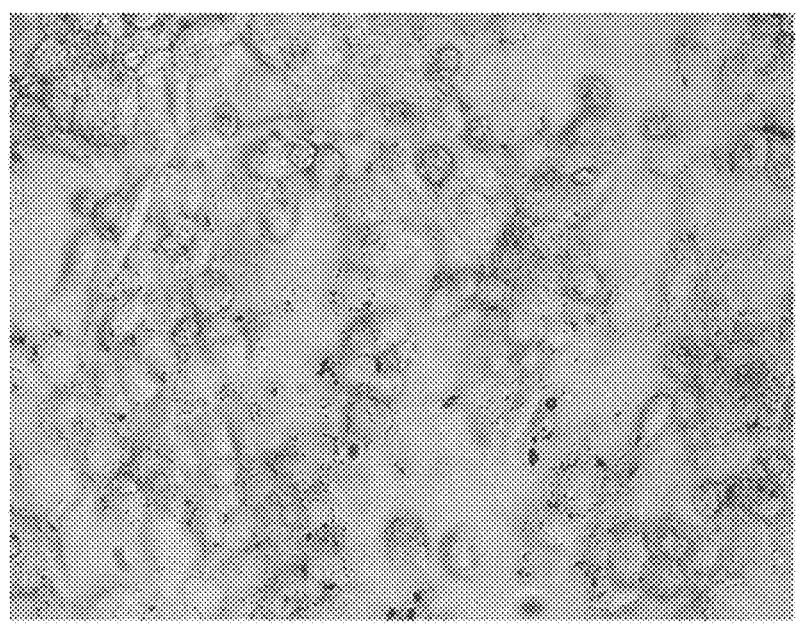
FIG. 5D is a photograph showing the macrophage phagocytosis of acetylated LDL inhibited by co-treatment of glycated HDL.

As shown in FIG. 4, it was confirmed that glycated HDL exhibited less than half of the activity of paraoxonase compared to native HDL, indicating that the functional damage of HDL was caused by glycation.

<2-2> Analysis of Early Response of Atherosclerosis (Macrophages Phagocytosis of Acetylated LDL)

The functional change in HDL by glycation was evaluated by analyzing the difference in preventive activity of native HDL and HDL glycation induction model against macrophage phagocytosis by acetylated LDL, an early response of atherosclerosis.

THP-1 cells, a human mononuclear cell line, were purchased from American Type Culture Collection (ATCC #TIB-202™) and maintained in RPMI1640 (Hyclone) supplemented with 10% fetal bovine serum (FBS). The cells grown in a 24-well plate with less than 20 passages were reacted with phorbol 12-myristate 13-acetate (PMA; final conc. 150 nM) for 48 hours at 37° C. in a humidified incubator (5% $CO_2$, 95% air) to induce differentiation into macrophages.

The differentiated macrophages were treated with acetylated LDL to induce phagocytosis while culturing, and at the same time, native HDL and glycated HDL were treated to compare the degree of preventive activity of macrophage phagocytosis. The degree of phagocytosis was compared through oil red O staining after fixing the cells, and the results are shown in FIG. 5.

As shown in FIG. 5, it was confirmed that phagocytosis of LDL was reduced by more than 60% when native HDL was co-treated compared to when acetylated LDL was treated alone, while phagocytosis was increased by 1.3 times when glycated HDL was co-treated compared to when native HDL was treated.

Figure 6:
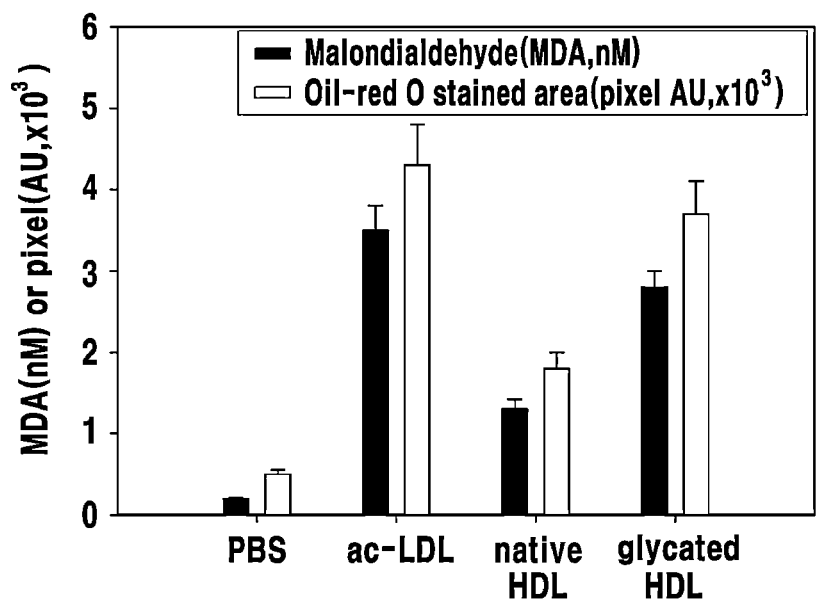
FIG. 6 is a graph expressing the amount of oxidized species detected in normal control cell culture medium, acetylated LDL-treated cell culture medium, acetylated LDL and native HDL co-treated cell culture medium, and acetylated LDL and glycated HDL co-treated cell culture medium as the amount of MDA (malondialdehyde).

On the other hand, the amount of oxides produced in cell culture media was compared by the thiobarbituric acid reaction quantification method. As a result, as shown in FIG. 6, the highest MDA (malondialdehyde) of 3.8 nM was detected when acetylated LDL was treated alone, while the lowest MDA of 1.3 nM was detected when native HDL was co-treated, and 2.8 nM of MDA was detected when glycated HDL was co-treated.

As shown in the results above, glycated HDL was found to have significantly reduced activity in preventing phagocytosis of acetylated LDL, which is an early response of atherosclerosis, confirming that the function of HDL was impaired by glycation.

Experimental Example 3: Comparative Evaluation of Cytotoxicity

By evaluating the cytotoxicity of native HDL and HDL glycation induction model, the effect of glycation on the cytotoxicity of HDL was evaluated.

Specifically, the cytotoxicity of native HDL and HDL glycation induction model was compared and evaluated by the MTT (3-(4,5-dimethylthiozol-2-yl)-3,5-diphenyl tetrazolium bromide) measurement method. African green monkey kidney cells (ATCC CRL-1586) were seeded in a 96-well cell culture plate at the density of $5 \times 10^4$ cells/well, cultured in a 37° C., 5% $CO_2$ incubator for 48 hours, obtained a cell monolayer, and washed twice with physiological saline. The plate was treated with each lipoprotein (100 µL/well) at each test concentration, and then cultured in a 37° C., 5% $CO_2$ incubator for 72 hours. After adding MTT solution to the plate (10 µL/well), it was allowed to stand in a 37° C., 5% $CO_2$ incubator for 4 hours, reacted for 4 hours, and then the formazane crystals were sufficiently dissolved, and then the absorbance was measured at 570 nm. The cytotoxicity ratio was calculated according to the following equation as the ratio of the experimental group treated with normal cells and lipoproteins, and the results are shown in FIG. 7.

Cell viability (%)=Test OD/Control OD×100%

Figure 7:
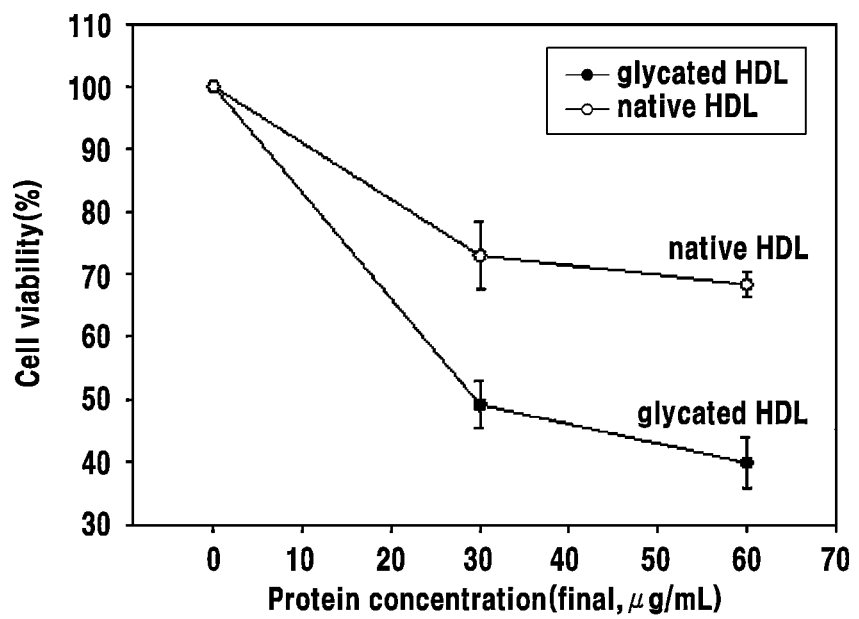
FIG. 7 is a graph showing the effect of native HDL and glycated HDL on the viability of African green monkey kidney cells.

As shown in FIG. 7, native HDL showed a cell viability of 68-73%, whereas glycated HDL showed a cell viability of 40-49%, confirming that the cytotoxicity of HDL was increased by glycation.

Experimental Example 4: Evaluation of Coronavirus Killing Activity

The killing ability of native HDL and HDL glycation induction model against coronavirus (SARS-Co-V-2) was compared and evaluated.

African green monkey kidney cells (ATCC CRL-1586) were seeded in a 96-well plate at the density of $5×10^4$ cells/well, and cultured in a 37° C., 5% $CO_2$ incubator for 48 hours. obtained a single layer of cells, and washed twice with physiological saline. After obtaining a cell monolayer, it was washed twice with physiological saline, and cell counting was performed. Thereafter, coronavirus (SARS CoV-2) was dispensed in the plate (100 µL/well) using DMEM (FBS free, 1% antibiotic-antimycotic) to be infected with 0.001 MOI, and then allowed to stand in a 37° C., 5% $CO_2$ incubator for 1 hour. After infecting for 1 hour, the virus was removed, and the culture medium containing the samples of native HDL and HDL glycation induction model prepared at the test concentrations was dispensed in the plate (100 µL/well), followed by culture in a 37° C., 5% $CO_2$ incubator for 72 hours. After checking the cell state, MTT solution was added to the plate (10 µL/well), and then the plate was allowed to stand in a 37° C., 5% $CO_2$ incubator for 4 hours. After 4 hours of the reaction, MTT solution was added to the plate (100 µL/well), formazan crystals were sufficiently dissolved using a pipette, and the absorbance was measured at 570 nm using a plate reader. The cytotoxicity ratio was calculated according to the following equation as the ratio of the experimental group treated with normal cells and lipoproteins, and the results are shown in FIG. 8.

Virus inhibition rate (%)=(Test OD-Virus OD)/(Control OD-Virus OD)×100%

As a result, when treated with 60 µg/mL, native HDL showed 62% SARS CoV-2 killing ability, whereas glycated HDL showed 17% SARS CoV-2 killing ability under the same conditions. These results indicate that native HDL has a 3.6-fold higher ability to kill SARS CoV-2 than glycated HDL.

Figure 8:
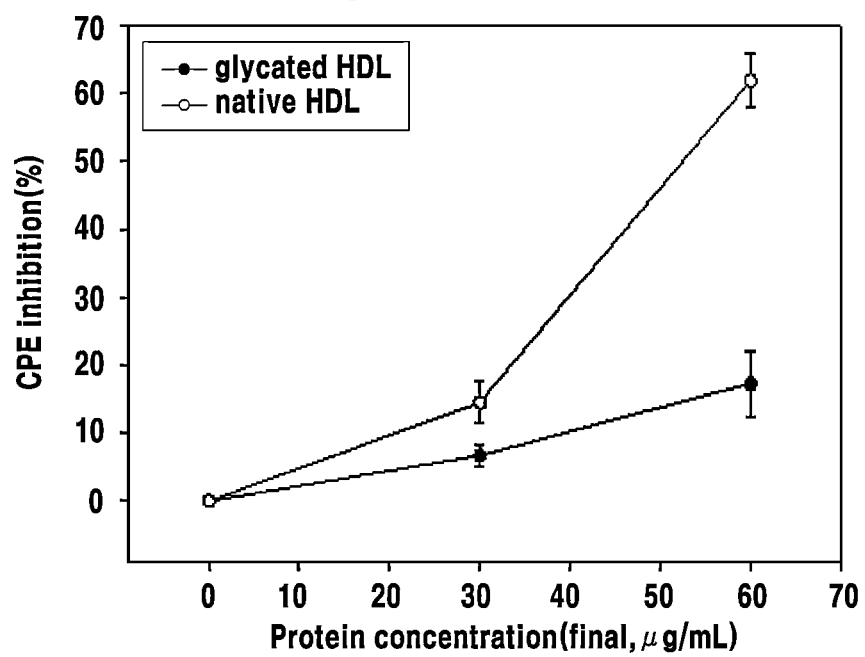
FIG. 8 is a graph showing the coronavirus killing effect of native HDL according to the present invention compared to that of glycated HDL.

As shown in FIGS. 7 and 8, when treated with native HDL, cytotoxicity was low, $CC_{50}$ was 79.4±1.5 µg/mL (final conc.: 2.8 µM), whereas $EC_{50}$ was 52.1±1.1 µg/mL (final conc.: 1.8 µM), confirming the excellent virus killing ability of native HDL against coronavirus (SARS-Co-V-2).

From the above results, it was confirmed that non-glycated native high-density lipoproteins (HDLs) can be provided as a pharmaceutical composition for preventing and treating corona19 disease (COVID-19). In addition, as identified by the present inventors, it can be used to explain why the risk and fatality rate of COVID-19 are higher in diabetics and hypertension patients who are concerned about impaired HDL structure and function, compared to normal people. This can be used for a method of providing information on the prognosis of COVID-19, and can also be used as a method for screening a pharmaceutical composition for preventing or treating COVID-19.

INDUSTRIAL APPLICABILITY

As identified by the present inventors, non-glycated normal high-density lipoproteins (HDLs) exhibit killing activity against coronavirus (SARS-Cov-2) that is superior to that of glycated HDLs, and thus a pharmaceutical composition for preventing and treating COVID-19, containing non-glycated native HDLs as an active ingredient, is provided. In addition, the present invention is useful since a method for maximizing the coronavirus killing activity by using an HDL glycation inhibitor, on the basis of the identification by the present inventors, can be provided and a method for screening for a pharmaceutical composition for preventing and treating COVID-19 by evaluating the degree of HDL glycosylation inhibition of candidate drugs can be provided.

What is claimed is:

1. A method for treating corona 19 infection (COVID-19) in a subject in need thereof, said method comprising administering non-glycated HDL (high-density lipoprotein) to the subject, wherein the non-glycated HDL has killing activity against coronavirus (SARS-Co-V-2), and wherein the non-glycated HDL is isolated from human serum and has a diameter of 18 to 21 nm.

2. The method for treating COVID-19 according to claim 1, wherein the non-glycated HDL increases paraoxonase activity compared to glycated HDL and decreases phagocytosis of LDL compared to glycated HDL.

* * * * *